(12) United States Patent
Scott

(10) Patent No.: US 7,134,435 B2
(45) Date of Patent: Nov. 14, 2006

(54) SLEEPING APPARATUS AND RELATED METHODS

(75) Inventor: Ruel W. Scott, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/691,127

(22) Filed: Oct. 22, 2003

(65) Prior Publication Data
US 2005/0087194 A1  Apr. 28, 2005

(51) Int. Cl.
*A61F 13/00* (2006.01)
(52) U.S. Cl. .................................... 128/846
(58) Field of Classification Search ............... 128/846, 128/100.1, 101.1, 845, 876, 869, DIG. 15; 602/5, 23, 61, 62, 67, 75, 19; 2/319, 338; 224/662
See application file for complete search history.

(56) References Cited

U.S. PATENT DOCUMENTS

| | | | |
|---|---|---|---|
| 5,207,635 A * | 5/1993 | Richards et al. ............... 602/19 |
| 5,357,981 A | 10/1994 | Eilam et al. | |
| 5,383,475 A | 1/1995 | Austin | |
| 5,645,080 A * | 7/1997 | Toso ........................... 128/876 |
| 5,651,763 A * | 7/1997 | Gates .......................... 602/19 |
| 5,893,365 A | 4/1999 | Anderson | |
| 6,137,675 A * | 10/2000 | Perkins ........................ 128/876 |
| 6,289,893 B1 | 9/2001 | Levitt | |
| 6,331,170 B1 * | 12/2001 | Ordway ........................ 602/19 |
| 6,357,444 B1 | 3/2002 | Parker | |
| 6,427,697 B1 * | 8/2002 | Pearcey ....................... 128/876 |
| 6,579,222 B1 * | 6/2003 | Mann ........................... 128/876 |
| 6,681,974 B1 * | 1/2004 | Rotter .......................... 224/662 |

OTHER PUBLICATIONS

Silverberg, D.S., et al., "Treating Obstructive Sleep Apnea Improves Essential Hypertension and Quality of Life," *American Family Physician*, vol. 65, No. 2, pp. 229-236, Jan. 2002.
Attarian, H.P., et al., "When to suspect obstructive sleep apnea syndrome," *Postgraduate Medicine*, vol. 111, No. 3, Mar. 2002.
Oksenberg, A., et al., "Positional vs Nonpositional Obstructive Sleep Apnea Patients: Anthropomorphic, Nocturnal Polysomographic, and Multiple Sleep Latency Test Date," *Chest*, vol. 112, No. 3, pp. 629-639, Sep. 1997.
Nakano, H., et al., "Effects of Body Position on Snoring in Apneic and Nonapneic Snorers," *Sleep*, vol. 26, No. 2, pp. 169-172, 2003.
Patel, A.T., et al., "Diagnosis and Management of Acute Low Back Pain," *American Family Physician*, 61:1779-86, 1789-90, Mar. 2000.
Hamza, M.A., et al., "Effect of the Duration of Electrical Stimulation on the Analgesic Response in Patients with Low Back Pain," *Anesthesiology*, vol. 91, No. 6, pp. 1622-1627, 1999.
Richards, K.C., "Sleep Promotion in the Critical Care Unit," *AACN Clinical Issues in Critical Care Nursing*, vol. 5, No. 2, pp. 152-158, May 1994.

(Continued)

*Primary Examiner*—Henry Bennett
*Assistant Examiner*—Dinnatia Doster-Greene
(74) *Attorney, Agent, or Firm*—Kagan Binder, PLLC

(57) ABSTRACT

Described are sleeping apparatus and related methods that involve a motion-limiting member, a therapeutic device, or both, positioned at the lumbar spine.

12 Claims, 5 Drawing Sheets

OTHER PUBLICATIONS

Richards, K.C., "Sleep Promotion," *Critical Care Nursing Clinics of North America*, vol. 8, No. 1, pp. 39-52, Mar. 1996.

Smith, W.A., "Fibromyalgia Syndrome," *Orthopedic Nursing*, vol. 33, No. 4, pp. 653-669, Dec. 1998.

* cited by examiner

SLEEPING APPARATUS AND RELATED METHODS

FIELD OF THE INVENTION

The invention relates to devices and apparatus worn near the lumbar spine during sleep. Embodiments of the device can be useful to allow or cause desired, non-supine sleep positioning, for example in individuals with any one or more of obstructive sleep apnea, snoring, or low back pain. Embodiments of the invention can be useful to alternatively or additionally provide one or more of types of therapy to the lumbar spine, such as thermo-regulatory therapy (including superficial heat, deep heat, and cold therapy), electrical neural stimulation therapy, and massage therapy, for example to individuals who suffer from anxiety related muscle tension.

BACKGROUND

Millions of Americans suffer from poor sleep hygiene or sleep impairment. Sleep impairment is frequently a result of multi-factorial somatic disturbances. Common causes of impaired sleep include obstructive sleep apnea, lower back pain, and anxiety.

Obstructive Sleep Apnea (OSA) is quite prevalent in the United States. Approximately ten percent of persons ages thirty through sixty (five percent of women and fifteen percent of men) have OSA. OSA has been associated with cardiovascular disease such as myocardial infarctions and arrhythmias, and increased risk of stroke. Experts suggest the possibility that sixty percent of patients with OSA have positional apnea. Patients with positional OSA may develop or exacerbate apnea episodes when lying on their backs (supine position). There is also evidence that patients with severe snoring increase their snoring episodes when lying on their backs.

Sleep devices have been produced to encourage non-supine sleep positioning. One example is a t-shirt that includes pockets sewn into the back of the t-shirt at the thoracic spine. The pockets can be filled with objects such as tennis balls or plastic tubes, to cause uncomfortable pressure when an individual is in the supine position. The uncomfortable pressure discourages the tendency to sleep in the supine position. Other examples of positional sleep devices have also been developed to encourage lateral or prone sleeping posture. Many of these devices use halter or harness or halter structures to position pads, pillows, or pouches along the thoracic spine.

Sleep hygiene can also be negatively impacted by lower back pain or general anxiety. Thus, individuals with back pain may benefit from thermal therapy or electrical nerve stimulation therapy, and individuals with anxiety may benefit from massage therapy, while sleeping.

SUMMARY

The invention relates to devices and apparatus that can provide improved sleep quality, improved sleep habits, and that can provide therapy to the lumbar spine, or two or more of these, to individuals with poor sleep quality related to a wide range of medical conditions. Specific conditions may include snoring, sleep apnea, muscle tension, stress, or combinations of two or more of these.

In one embodiment, the invention relates to a motion-limiting member positioned at a person's lumbar spine while sleeping. The motion-limiting member can provide positional restraint, for example, to individuals diagnosed with obstructive sleep apnea or severe snoring. The complications of obstructive sleep apnea or severe snoring are significantly worse in a supine position. A motion-limiting member of the invention, therefore, can prevent sleep in a supine position. The motion-limiting member generally can include an elongated pad or other such structure sized and positioned at the lumbar spine so a person sleeping on his or her side is substantially prevented from rolling onto his or her back.

The motion-limiting member may be part of a larger apparatus that could be, for example, a waist belt, a waistband for a lower body apparel such as shorts or pants, or the like. In preferred apparatus, a waist belt or a lower body apparel may include structure or material that maintains the position of the motion-limiting member during sleep, to prevent movement of the motion-limiting member out of a position at the lumbar spine that prevents a supine sleeping position. Exemplary embodiments of such structure or material may include a rigid structure such as an elongated rigid plate extending along a length of the belt or elastic material.

In other embodiments, the invention can relate to a therapeutic device positioned at a person's lumbar back, e.g., as part of a belt, a pad, lower body apparel, or in combination with a motion-limiting member. Such a device may be removable or changeable within a sleeping apparatus. A therapeutic device may include a heating or cooling device such as a thermo-regulatory pad to provide therapy in the treatment of low back pain. A thermo-regulatory pad may generate or store heat or cold, for example in the form of a cold pack, a resistive heater, a deep heating device, or the like. A therapeutic device may alternatively or additionally include an electrical nerve stimulation device as a treatment for lower back pain. Also alternatively or additionally, a therapeutic device may include a vibrating massage pad to deliver relaxation therapy for individuals with anxiety-related muscle tension. Any of the therapeutic devices may be adjustable using electronic controls or timing devices that will deliver therapy over a set period.

An aspect of the invention relates to an apparatus for preventing a sleeping person from assuming a supine position. The apparatus includes a flexible, elongated waist belt having a first surface, a second surface opposite the first surface, and a sufficient length to encircle the waist of a person, and a motion-limiting member protruding from the first surface of the belt and extending along at least a portion of the length of the belt. The motion-limiting member comprises a body of a size sufficient to prevent a person from moving into the supine position during sleep when the motion-limiting member is located proximal to the lumbar spine area.

Another aspect of the invention relates to an apparatus that includes lower body apparel. The lower body apparel includes a waist belt and a motion-limiting member extending proximal to a length of the waist belt so that when the lower body apparel is worn by a person, the motion-limiting member is located along a lumbar portion of the spine.

Still another aspect of the invention relates to a method of preventing a person from assigning a supine position during sleep. The method includes providing an apparatus including a flexible, elongated waist belt having a first surface, a second surface opposite the first surface, and a sufficient length to encircle the waist of a person, and a motion-limiting member protruding from the first surface of the belt and extending along at least a portion of the length of the belt. The belt is secured around the waist of the body so the motion-limiting member is located proximal to the lumbar region of the person. The apparatus is worn during sleep.

Yet another aspect of the invention relates to a sleep apparatus and related methods of use. The sleep apparatus includes a flexible, elongated waist belt having sufficient length to encircle the waist of a person, and a therapeutic device located along at least a portion of the length of the belt, wherein the therapeutic device is sized and positioned to provide therapy to the lumbar spine area.

DETAILED DESCRIPTION

The invention relates to sleeping apparatus that include a portion of the apparatus worn at the lumbar spine while sleeping. As will be understood, the "lumbar spine" refers to the area over the lower back that includes at least some of the bi-lateral, supergluteal, "lumbar" area.

The sleeping apparatus may include one or multiple components designed to improve sleep hygiene or sleep quality, the component or components positioned at the lumbar spine. Examples include a motion-limiting member, one or more therapeutic devices, or a combination of a motion-limiting member and one or multiple therapeutic devices. Examples of therapeutic devices include a thermo-regulatory device such as a superficial heating device (e.g., a heating pad device); a deep-heating device (e.g., a shortwave diathermy, microwave diathermy, or ultrasound device); a cooling device; a vibrating massage device; a neural stimulation unit (e.g., transcutaneous electrical neural stimulation, or "TENS"), or combinations of these.

A specific example of a motion-limiting member can be a longitudinal-shaped structure that is permanently or removably attached to a belt or belt-like structure ("belt"). The belt can be a flexible, elongate waist belt having first and second opposing surfaces, and can be of a sufficient length to be worn around a person's waist so that a portion of the length of the belt is positioned over the lumbar spine. According to embodiments of the invention, that portion can include a motion-limiting member.

Specific features of a motion-limiting member include a structure protruding from a surface of the belt and extending along at least a portion of the length of the belt, wherein the motion-limiting member comprises a body of a size sufficient to prevent a person from moving into the supine position during sleep when the motion-limiting member is worn proximal to the lumbar spine area. The size and physical properties of the motion-limiting member, such as stiffness, can prevent the wearer from achieving a supine position during sleep.

Figure 3:
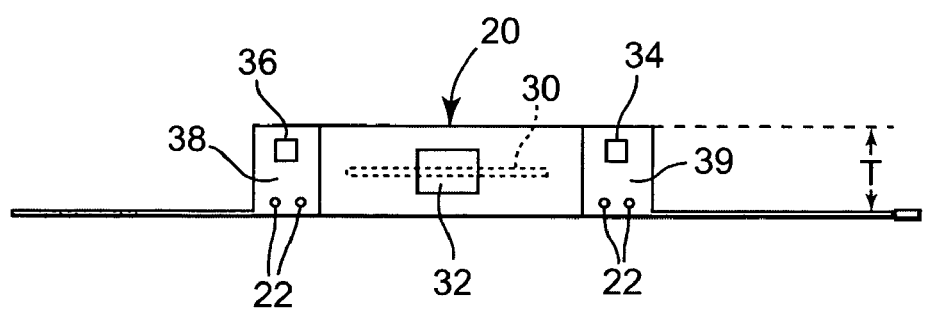
FIG. 3 is a side view of the apparatus of FIG. 2.

An example of a useful size and shape of a motion-limiting member can be a member extending along a length of a belt, for positioning over the lumbar spine when the belt is worn around the waist, and having a length, thickness, thickness, and physical properties (e.g., hardness, density, etc.) that prevent the wearer from achieving the supine position during sleep. Thickness (T) refers to the distance that the member extends from the belt (see FIG. 3). The thickness can be any thickness that is useful to accomplish the function of preventing a sleeper from assuming a supine position. A thickness of any specific apparatus can depend on factors such as the stiffness or rigidity of the motion-limiting member or portions of the member, as well as the length of the member, or the size (e.g., weight or waist size) of the wearer. A useful thickness may be from 1 to 12 inches, extending from the belt, e.g., from 2 to 6 or from 3 to 6 inches.

The length of the motion-limiting member can be any length that is useful to prevent a wearer from assuming the supine position during sleep. Examples may be from 8 to 20 inches along a length of a belt, preferably from 12 to 20 inches.

The width (W) of the motion-limiting member can be any useful width, such as about the same "width" as a standard or relatively large waist belt or waist band of a lower body apparel, e.g., from about 3 to about 6 or 8 inches.

A motion-limiting member can be constructed of one or more different materials that are useful, alone or in combination, to prevent a wearer from assuming the supine position during sleep. The member can be a single piece of a relatively stiff, optionally flexible foam, rubber, cloth, stuffing, plastic, Styrofoam, or wood, optionally contained in a cloth or leather covering or container that may also optionally include one or more layers of padding.

Embodiments of a motion-limiting member can include a uniform or substantially uniform make-up along the length of the member, of sufficient size and stiffness to prevent the wearer from assuming the supine position. In such an embodiment, the motion-limiting member may be prepared from a single or multiple pieces of relatively stiff, rigid material such as a relatively stiff foam, rubber, plastic, Styrofoam, wood, or the like. A high strength to weight ratio such as can be exhibited by these materials, is desirable. As a single example, the member may be in the form a foam, rubber, or plastic elongate block of material, optionally including an outer layer of padding or a covering such as a cloth or leather covering.

Other embodiments of a motion-limiting member may include multiple segments (e.g., separate block-like segments) made of the same or different materials, located, preferably adjacent to one another, along the length of the belt. As a specific example, a motion-limiting member may include three separate, adjacent segments including two end segments and a middle segment between the end segments.

Each end segment may preferably be of a relatively stiff, rigid material such as a relatively stiff foam, rubber, plastic, Styrofoam, wood, or the like. The middle segment may be relatively more flexible or pliable material, such as a gel or spongy foam. Each segment may optionally be separately covered by a layer of padding or a cloth or leather covering, or two or more (e.g., all) segments may be contained within the same layer or layers of padding or leather, cloth, or plastic covering. More than three segments may also be useful. The use of three segments, including relatively more rigid end segments and a less rigid middle section, can allow the end sections to prevent the wearer from assuming a supine position, while the middle section allows an amount of motion or flexibility of the member between the end segments.

Embodiments of motion-limiting members can include various useful structures that cooperate with a belt, a lower body apparel, or a therapeutic device, to improve one or more of positioning of a therapeutic device, positioning of a motion-limiting member, or that perform a function useful for a desired therapy. As an example, a motion-limiting member may include fasteners for removably attaching a motion-limiting member or a therapeutic device to a belt. Fasteners may be in the form of snaps, Velcro, a zipper mechanism, or other useful fasteners. A fastener can cooperate with a corresponding fastener at one or both opposing surfaces of the belt, e.g., a motion-limiting member or a therapeutic device may include fasteners or a fastening mechanism that wraps around the width of the belt. Additionally, in certain embodiments of apparatus that include a neural stimulation device, a fastener may be conductive and may be located at a surface of the belt to contact a wearer's skin. Such a conductive fastener may connect electrically to the neural stimulation device and can thereby function as an electrode for contacting skin at the lumbar spine to effect neural stimulation.

As another example, a motion-limiting member may include an internal or external location for receiving a therapeutic device, such as a zippered compartment that receives one or more of a therapeutic device, batteries, and associated electronic controls. Alternatively, electronic controls may be received by or integral to one or more segments of a multi-segment motion-limiting member, such as within relatively rigid end segments, while a therapeutic device such as a massage device, heating or deep-heating device, cold pack, neural stimulator device, etc., may be interchangeably located inside a middle segment or multiple segments between the end segment.

The belt can be of an elastic or inelastic material such as leather, plastic, or a fabric that includes elastic such as an elastic waistband, and can include size-adjusting structure such as a buckle. The belt can optionally substantially exclude pendant or appurtenant structures such as a harness, halter, or similar such additional elongate belt-like structures designed to secure the primary belt in place or maintain its position during sleep. Still, embodiments of the belt may be integral to or removable from a piece of apparel such as shorts, pants, or a shirt. Also, the belt, on either side, can include fasteners that correspond to fasteners on the motion-limiting member, for removably fastening the motion-limiting member to the belt.

One embodiment of a belt can include substantially only a belt that preferably excludes other structure such as harnesses or appurtenant structure, in combination with an integral or removable motion-limiting member. Another embodiment of the belt can be an elastic or inelastic waistband of an item of lower body apparel such as pants or shorts.

The apparatus can include one or multiple features or structures that limit the movement of the apparatus while worn during sleep. A belt worn around the waist, especially if it includes a motion-limiting member or therapeutic device protruding at the lumbar spine, may tend to turn and rotate around the wearer at the waist, during sleep. The apparatus may optionally include one or more feature or features (e.g., a "motion-preventing feature) that can prevent such movement of a belt around the waist of the wearer.

One example of a useful motion-preventing feature can be a rigid member that cannot turn past the lateral waist when secured to a belt worn around the waist. A rigid member may take the form of a relatively rigid motion-limiting member, i.e., a motion-limiting member that is sufficiently rigid and sized (e.g., long enough) that when secured to a belt worn around a waist with the member at the lumbar spine, the belt cannot be turned to position the member at the front of the wearer (i.e., over the stomach). A rigid member may also take the form of a separate plate located along a length of the belt, e.g., positioned at the lumbar spine when worn. The plate can be of a sufficient length to prevent turning of the belt (when worn) around the side of a wearer's waist, to prevent turning of the plate from the lumbar spine around the side of the wearer's waist to the front abdominal position (stomach), thereby preventing movement from the lumbar spine.

A rigid member can be constructed of a material or materials sufficiently stiff and rigid to prevent a rotating motion of the belt when worn, such as a metal or relatively stiff plastic or polymeric material. As an example, a plate may be a stiff metal or plastic plate of a length that is similar to the length of the motion-limiting member, such as from 8 to 12 inches in length. The plate can be of a width equal or similar to the width of the belt, e.g., from 1 to 6 inches, or of a width that is slightly smaller than the width of the belt itself. The plate may be attached to the belt at either surface—the plate may be located at the belt surface toward the wearer, or away from the wearer between (e.g., between the belt and a therapeutic device or motion-limiting member). Optionally, the plate may be located on or interior to a motion-limiting member or an assembly that contains a therapeutic device.

Another example of a motion-preventing feature can be in the form of an item of lower body apparel. The apparel may be integrally or removably attached to a motion-limiting member (with our without a rigid plate as described above), and preferably can also be integrally or removably attached to a belt, e.g., in the form of a waistband or a separate belt that can be held to the waist of the apparel through loops or other fasteners. To prevent the motion-limiting member from moving to a position that is not effective to prevent the wearer from assuming a supine position during sleep, the apparel may include a relatively tight fitting elastic or inelastic material such as relatively tight-fitting elastic shorts. The elasticity of the shorts can preferably be sufficient to prevent movement of the member without causing discomfort.

Embodiments of apparatus of the invention include a therapeutic device to provide therapy to the lumbar spine. The therapeutic device is located at the lumbar spine while sleeping. The therapeutic device may be a component of an apparatus in combination with a motion-limiting member, or an apparatus of the invention may include a therapeutic device for positioning at the lumbar spine in the absence of a motion-limiting member. Examples of therapeutic devices include a thermo-regulatory device such as a superficial heating device (e.g., a heating pad device); a deep-heating (e.g., a shortwave diathermy, microwave diathermy, or ultrasound device); or a cooling device; a vibrating massage device; a neural stimulation unit (e.g., transcutaneous electrical neural stimulation, or "TENS"), or combinations of these.

A thermo-regulatory device can be an electric heating device, a cold-pack or a deep-heating device with ultrasound. Such devices are known to those of skill in the relevant therapeutic arts. An electric heating device may include a resistive heater useful to provide a therapeutic degree of heating, such as an amount useful to soothe muscular tension or cramps.

An electric massage device may include a device that provides a desired massaging effect, optionally with heat.

A deep-heating device can be a device such as is known in the heating therapy arts, that provides "deep-heating" in the form of one or more of a shortwave diathermy device, a microwave diathermy device, or an ultrasound device. Deep-heat causes a temperature rise from the conversion of energy into heat as energy penetrates the tissues of the body where the energy is applied, e.g., the lumbar spine. Energy sources include (1) high-frequency currents (shortwave diathermy), (2) electromagnetic radiation (microwaves), and (3) ultrasound (high-frequency sound).

A neural stimulator unit (e.g., TENS) can be incorporated into a sleeping apparatus of the invention. As is known, TENS neural stimulators can relieve pain by sending gentle electrical impulses through the skin to the nerves to suppress pain by blocking pain signals before they reach the brain. TENS sends these gentle impulses through lead wires that are connected to electrodes, which, according to the invention, can be placed at the lumbar spine. Thus, a TENS device as part of a sleep apparatus of the invention can provide relief from pain while sleeping, such as relief from lower back pain, surgery, traumatic injury, etc. The electrodes can be any form of electrode attendant to a neural stimulator unit or the larger sleep apparatus. For example, electrodes can be attached to wires and fixed to a surface of the belt at locations that provide desired contact for neural stimulation. In a particular embodiment, electrodes can be incorporated into conducting fasteners that attach to a surface of the belt that positions the fasteners to contact the skin and act as a conducting electrode for neural stimulation. One or two or more sets of electrodes may be included to allow for various forms of neural stimulation (e.g., pulsed).

A therapy device such as a thermo-regulatory device, massage device, or neural stimulator unit, may be powered by direct current (e.g., batteries) or alternating current such as by an electrical outlet. A device may be removably attached to the apparatus by use of a zipper, a zippered pouch, snaps, Velcro, or similar fastening devices, and may optionally include electronic controls such as variable heat settings or a timing device.

Exemplary embodiments of apparatus of the invention are illustrated in the accompanying figures. These are understood to be exemplary configurations of apparatus that include features of the invention, not to be construed as limiting the broader concepts embodied by the present description or claims.

Figure 1:
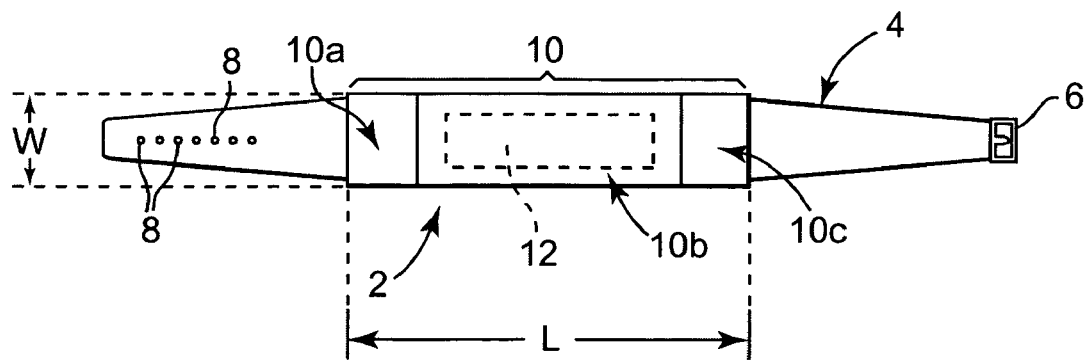
FIG. 1 is a front view of an apparatus of the invention having a belt structure and showing a motion-limiting member and a restrictor plate.

Referring to FIG. 1, a front view of an embodiment of a basic apparatus of the invention is shown. Apparatus 2 includes an elongate belt structure 4 that is of a length L and width W to be worn around a person's waist. A buckle 6 and holes 8 allow adjustment for waist size. Motion-limiting member 10 (including three segments, end segments 10a and 10c, and middle segment 10b) is located along a central length of the belt so the member is positioned at the lumbar spine when the belt is fastened around a wearer's waist. The illustrated embodiment of apparatus 2 of FIG. 1 includes a restrictor plate 12 of a length and width that is slightly smaller than the length L and width W of the motion-limiting member.

Figure 2:
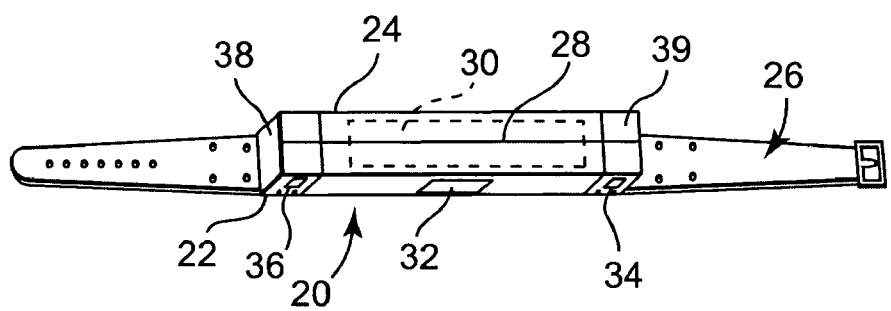
FIG. 2 is a perspective view of an apparatus of the invention having a belt structure and showing a motion-limiting member and a therapeutic device.

FIG. 2 illustrates a similar apparatus 20 that includes belt 26 that includes fasteners 22 for removably attaching motion-limiting member 24 to a surface of the belt 26. The fasteners may be snaps, Velcro, zippers, or the like. As shown, the apparatus 20 includes first and second support blocks 38 and 39 (e.g., end segments) for positioning the motion-limiting member 24 and for housing controls as described below. Motion-limiting member 24, in this embodiment, includes a therapeutic device 30 that can be inserted through zipper 28, to be located at the interior of member 24. The therapeutic device 30 that is illustrated includes a massage pad and a neural stimulator. Additional or different therapeutic devices may be used instead. The therapeutic device 30 is powered by batteries 32, and controlled by separate massage pad controls 34 and TENS pad controls 36. See also FIG. 3, which shows a side view of apparatus 20.

Figure 4:
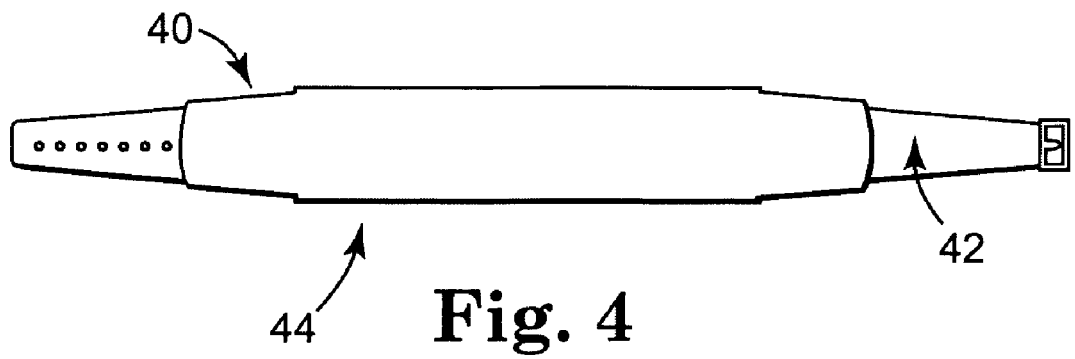
FIG. 4 is a front view of an apparatus of the invention showing a belt and an interchangeable pad.
Figure 5:
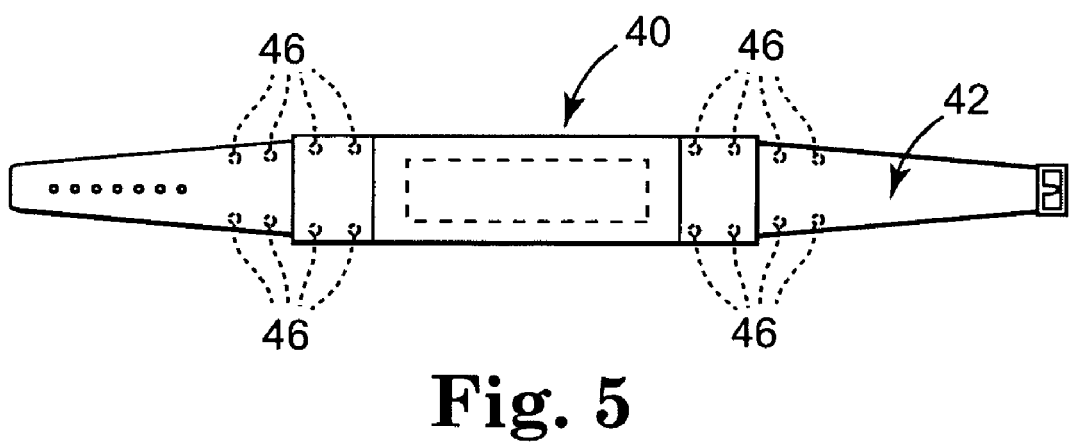
FIG. 5 is a front view of the belt from the apparatus shown in FIG. 4 illustrated without the interchangeable pad.
Figure 6:
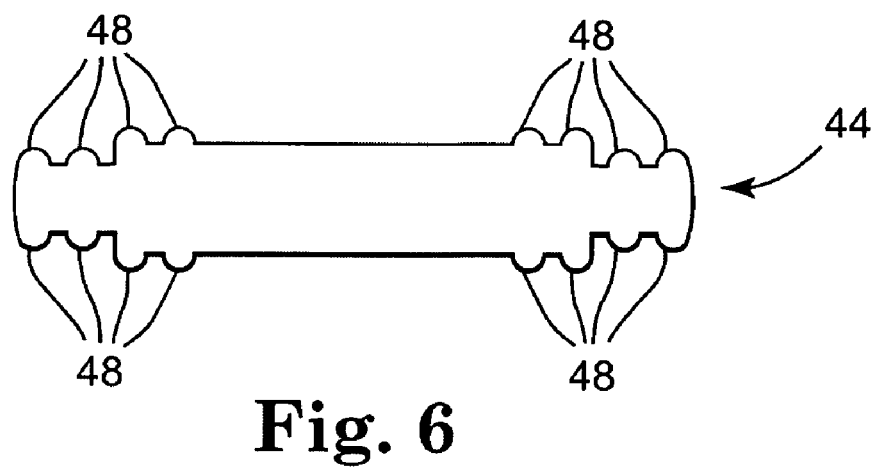
FIG. 6 is a front view of the interchangeable pad from the apparatus shown in FIG. 4 illustrated without the belt.

FIG. 4 illustrates features of an apparatus 40 that includes a belt 42 and a removable, interchangeable pad 44. Pad 44 may be of a size and composition to function as a motion-limiting member. Alternatively or additionally, pad 44 may include a therapeutic device (not shown), e.g., internal to pad 44, such as one or more of a thermo-regulatory pad device, a massage vibratory pad device, or an electrical stimulation pad. Also, batteries or another power source or electronic controls (not shown) can be present at the pad. FIG. 5 shows belt 42 with interchangeable pad 44 removed and FIG. 6 shows the interchangeable pad 44 without the belt 42. Belt 42 includes fasteners 46 (e.g., Velcro), which correspond to fasteners 48 (Velcro) of the pad 42. The pad 44 can be attached and removed from the belt 42 accordingly.

Figure 7:
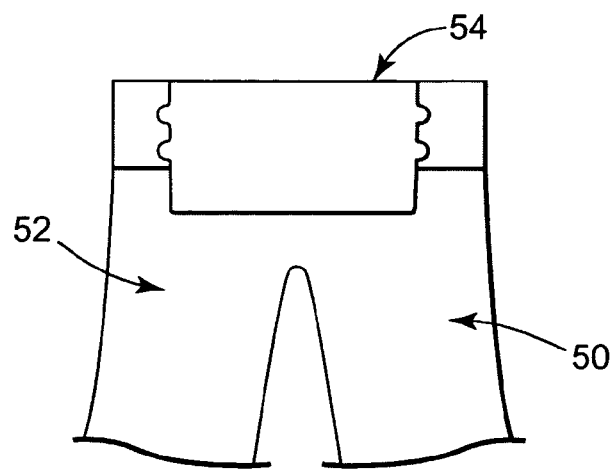
FIG. 7 is a rear view of a lower body apparel apparatus of the invention showing lower body apparel and an interchangeable pad.
Figure 8:
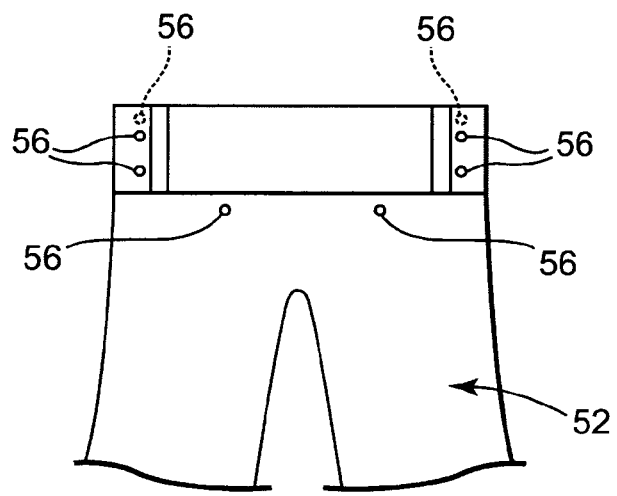
FIG. 8 is a rear view of the lower body apparel apparatus of FIG. 7 illustrated without the interchangeable pad.
Figure 9:
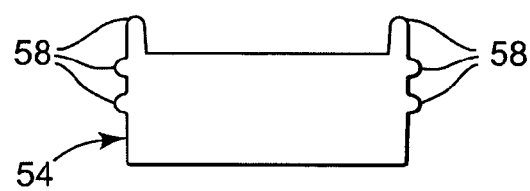
FIG. 9 is a front view of the interchangeable pad from FIG. 7 illustrated without the lower body apparel apparatus.

FIG. 7 shows a rear view of a lower body apparel device 50 in accordance with the present invention. The lower body apparel device 50 includes lower body apparel 52, such as shorts as shown, and an interchangeable pad 54 removably attached to the lower body apparel 52. FIG. 8 shows the lower body apparel 52 with the interchangeable pad 54 removed, and FIG. 9 shows the interchangeable pad 54 without the lower body apparel 52. The lower body apparel and pad can include one or more of the therapeutic devices described herein, e.g., internal or external to the pad, at a location to provide one or more therapies to the lumbar spine areas. As shown, lower body apparel 52 includes Velcro fasteners 56, which correspond to Velcro fasteners 58 of the interchangeable pad 54.

Figure 10:
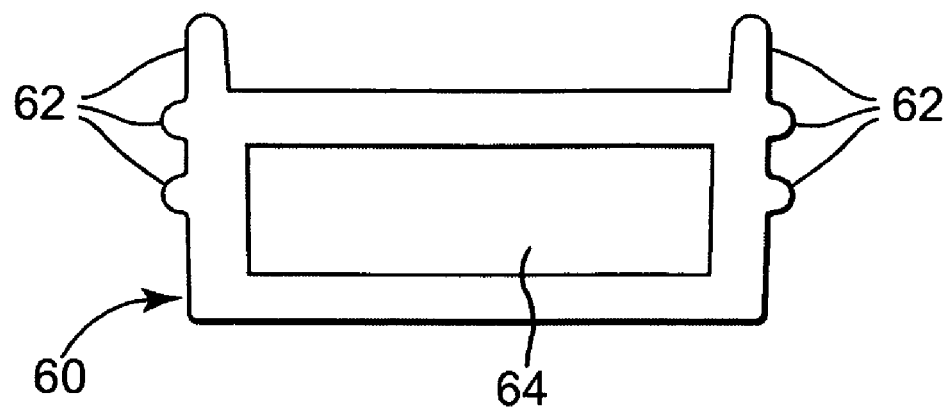
FIG. 10 is a front view of an interchangeable pad of the invention.

FIG. 10 illustrates an interchangeable pad 60 that may be used in place of the interchangeable pad 54 in the lower body apparel device 50. As shown in FIG. 10, interchangeable pad 60 includes fasteners 62 for attaching the interchangeable pad 60 to fasteners 56 of the lower body apparel 52. Interchangeable pad 60 also includes an opening 64 for receiving a therapeutic device (not shown). The therapeutic device can be removably installed into the opening 64. The pad can be configured to receive any one or more of different types of therapeutic devices, including one or more of a thermo-regulatory pad, a massage vibratory pad, or an electrical stimulation pad.

Figure 11:
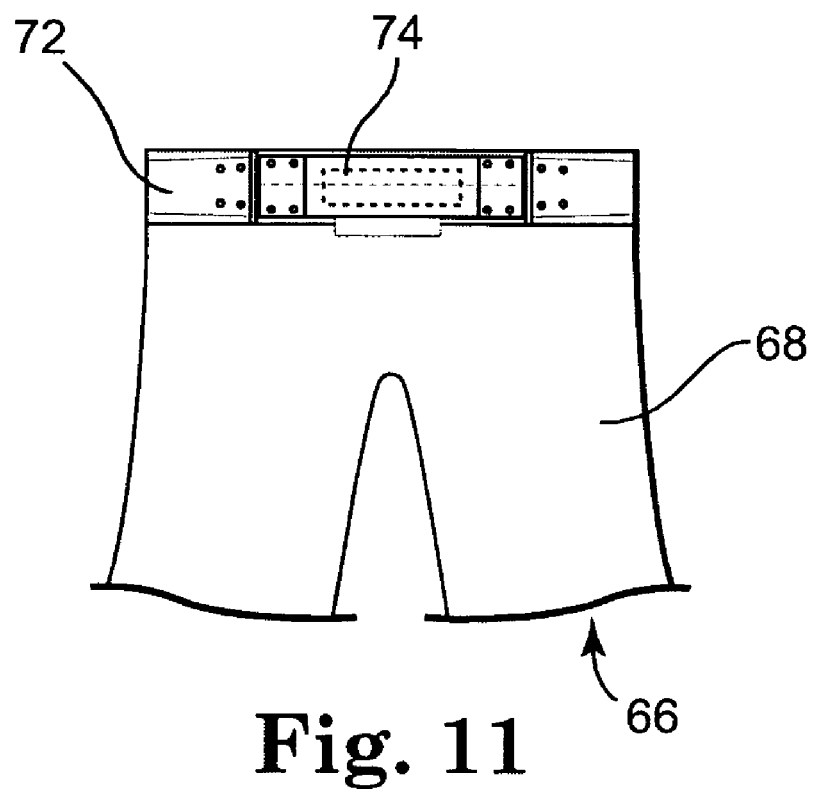
FIG. 11 is a rear view of lower body apparel of the invention.
Figure 12:
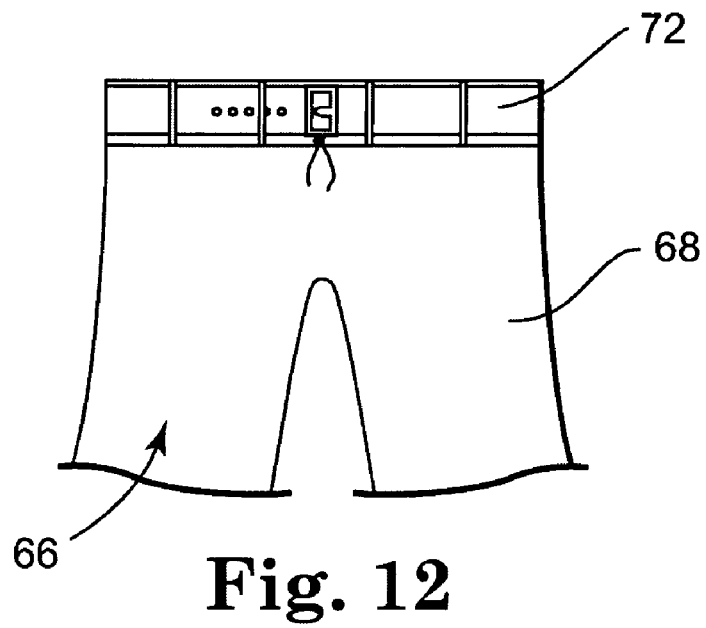
FIG. 12 is a front view of the lower body apparel of FIG. 11.
Figure 13:
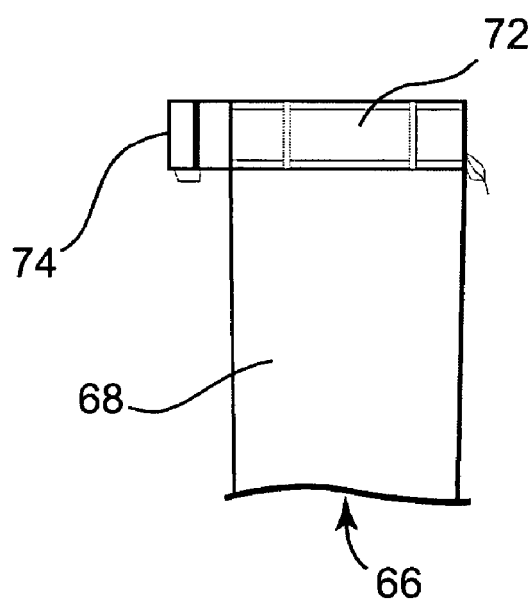
FIG. 13 is a left side view of the lower body apparel of FIGS. 11 and 12.

FIG. 11 illustrates a rear view of a lower body apparel assembly 66. In FIG. 12, a front view of the lower body apparel assembly 66 is shown and in FIG. 13 a left side view of the lower body apparel assembly 66 of FIGS. 11 and 12 is shown. As shown, the lower body apparel includes lower body apparel 68, belt 72, and motion-limiting member 74.

The apparatus of the invention may be worn during sleep to improve sleep hygiene, to improve sleep quality, to provide therapy during sleeping, or combinations of these, by positioning the sleep apparatus at the lumbar spine. For example, an apparatus of the invention that includes a motion-limiting member worn at the lumbar spine can be worn during sleep to prevent the wearer from assuming the supine position during sleep, which can prevent apnea and snoring. Alternatively or in addition, an apparatus of the invention that includes a therapy device worn at the lumbar spine can be worn during sleep to provide heating or cooling to the lumbar spine, massage, neural stimulation, or deep-heating therapy. One or more of these may be used in combination to treat any one or more of low back pain, muscle tension, anxiety-related tension, muscle injury, etc., optionally improving sleep quality.

As an example of an method of using an apparatus, a basic apparatus that includes a belt and motion-limiting member, absent any therapeutic device, can be used by individuals to improve sleeping positioning, to prevent the sleeper from assuming a supine position, and to thereby treat sleep apnea or severe snoring. No therapeutic device, electronic controls, or batteries, are included in the apparatus.

As another example of an method of using an apparatus, a basic apparatus that includes a belt and therapeutic device can be used by individuals to improve sleeping comfort or to treat or relieve a condition such as muscle tension, anxiety, lower back pain or injury, etc. The apparatus can include a belt, optionally in combination with a lower body apparel, and need not include a motion-limiting member. The apparatus may include a pad or other structure or member that positions the therapeutic device at the lumbar spine when the apparatus is worn. An example may be a zippered foam pad that receives a therapeutic device, batteries, and electronic controls. Electrodes for a neural stimulation device may be included and positioned to contact the wearer's skin at one or multiple pairs of positions at the lumbar spine.

As another example of a method of using an apparatus, an apparatus can include a combination of a motion-limiting member and one or multiple therapeutic devices Such an apparatus can be used to treat individuals having two or more conditions that compromise sleep quality, such as positional obstructive sleep apnea, severe intolerable snoring, low back pain, and anxiety with muscle tension. Such an apparatus can improve sleeping comfort by treating a lower back condition, while at the same time improving sleep positioning to prevent the sleeper from assuming a supine position and to thereby treat sleep apnea or severe snoring. Low back pain can be treated by a thermo-regulatory device or electrical nerve stimulation device of the apparatus. Anxiety related muscle tension can be treated by a massage device of the apparatus. Any one or more of these therapeutic devices and associated controls and batteries can be received by the motion-limiting member.

Preferred embodiments of the methods and apparatus according to the invention are described herein. Variations on the preferred embodiments will become apparent to those of skill in the relevant arts upon reading this description. The inventors expect those of skill to use such variations as appropriate, and intend for the invention to be practiced otherwise than specifically described herein. Accordingly, the invention includes all modifications, combinations, and equivalents of the subject matter recited in the claims as permitted by applicable law. Moreover, any combination of the above-described elements in all possible variations thereof is encompassed by the invention unless otherwise indicated.

The invention claimed is:

1. An apparatus for preventing a sleeping person from assuming a supine position, the apparatus comprising:
   a flexible, elongated waist belt having a first surface, a second surface opposite the first surface, and a sufficient length to encircle the waist of a person, and
   a motion-limiting member protruding from the first surface of the belt and extending along at least a portion of the length of the belt, wherein the motion-limiting member comprises a body of a size sufficient to prevent a person from moving into the supine position during sleep when the motion-limiting member is located proximal to the lumbar spine area and wherein the motion-limiting member comprises at least three body segments including a middle body segment and two end body segments at opposite sides of the middle body segment, wherein the end body segments are more rigid than the middle body segment.

2. The apparatus of claim 1 wherein the motion-limiting member comprises first and second side surfaces extending from the belt, the first and second side surfaces having a thickness extending at least three inches from the belt.

3. The apparatus of claim 2 wherein the motion-limiting member has a length in the range from 8 to 20 inches and the first and second side surfaces have a thickness extending from 3 to 6 inches from the belt.

4. The apparatus of claim 1 wherein the end body segments comprise rigid supportive material and the middle body segment comprises soft pliable material.

5. The apparatus of claim 1 comprising a rigid plate positioned along a length of the belt proximal to the motion-limiting member, wherein the plate is positioned and sized to prevent movement of the motion-limiting member during sleeping.

6. The apparatus of claim 1 comprising lower body apparel wherein the belt comprises a waistband attached to the lower body apparel and the motion-limiting member comprises a pad detachable from the lower body apparel.

7. The apparatus of claim 1 comprising a nerve stimulation device, a thermo-regulatory device, a deep-heating device with ultrasound, a massage device, or a combination two or more of these.

8. An apparatus comprising lower body apparel comprising a waist belt and a motion-limiting member extending proximal to a length of the waist belt so that when the lower body apparel is worn by a person, the motion-limiting member is located along a lumbar portion of the spine and comprising a nerve stimulation device with conductive electrodes,
   wherein the motion-limiting member comprises a pad that is detachable from the waistband using fasteners.

9. The apparatus of claim 8 wherein when the apparel is worn, the motion-limiting member prevents the person from assuming a supine position during sleep.

10. An apparatus for preventing a sleeping person from assuming a supine position, the apparatus comprising:
    a flexible, elongated waist belt having a first surface, a second surface opposite the first surface, and a sufficient length to encircle the waist of a person;

a motion-limiting member protruding from the first surface of the belt and extending along at least a portion of the length of the belt, wherein the motion-limiting member comprises a body of a size sufficient to prevent a person from moving into the supine position during sleep when the motion-limiting member is located proximal to the lumbar spine area; and a rigid plate positioned along a length of the belt proximal to the motion-limiting member, wherein the plate is positioned and sized to prevent movement of the motion-limiting member during sleeping.

11. An apparatus for preventing a sleeping person from assuming a supine position, the apparatus comprising:

a flexible, elongated waist belt having a first surface, a second surface opposite the first surface, and a sufficient length to encircle the waist of a person;

a motion-limiting member protruding from the first surface of the belt and extending along at least a portion of the length of the belt, wherein the motion-limiting member comprises a body of a size sufficient to prevent a person from moving into the supine position during sleep when the motion-limiting member is located proximal to the lumbar spine area; and lower body apparel wherein the belt comprises a waistband attached to the lower body apparel and the motion-limiting member comprises a pad detachable from the lower body apparel.

12. An apparatus comprising lower body apparel comprising a waist belt and a motion-limiting member extending proximal to a length of the waist belt so that when the lower body apparel is worn by a person, the motion-limiting member is located along a lumbar portion of the spine wherein the motion-limiting member comprises a pad that is detachable from the waistband using fasteners.

* * * * *